United States Patent [19]

Merkatoris

[11] Patent Number: 4,711,683

[45] Date of Patent: Dec. 8, 1987

[54] METHOD AND APPARATUS FOR MAKING ELASTIC DIAPERS

[75] Inventor: John R. Merkatoris, Green Bay, Wis.

[73] Assignee: Paper Converting Machine Company, Green Bay, Wis.

[21] Appl. No.: 23,136

[22] Filed: Mar. 9, 1987

[51] Int. Cl.$^4$ .............................................. B32B 31/08
[52] U.S. Cl. ..................... 156/164; 118/300; 118/326; 156/229; 156/291; 156/301; 156/356; 239/297; 427/273; 427/348
[58] Field of Search ............... 156/164, 229, 291, 301, 156/356, 495, 494, 498, 578; 239/84, 99, 291, 296, 297, 298, 300, 301; 118/300, 301, 326; 427/282, 273, 348, 420

[56] References Cited

U.S. PATENT DOCUMENTS

| | | | |
|---|---|---|---|
| 3,294,058 | 12/1966 | Shriro | 118/301 |
| 3,661,679 | 5/1972 | Law | 156/578 |
| 3,785,898 | 1/1974 | Gerber et al. | 156/356 |
| 3,900,639 | 8/1975 | Lauterbach | 427/348 |
| 4,064,295 | 12/1977 | Singer | 427/424 |
| 4,081,301 | 3/1978 | Buell | 156/229 |
| 4,128,667 | 12/1978 | Timson | 427/420 |
| 4,300,967 | 11/1981 | Sigl | 156/164 |
| 4,353,762 | 10/1982 | Bouda | 156/164 |
| 4,376,670 | 3/1983 | Rodish | 156/356 |
| 4,417,935 | 11/1983 | Spencer | 156/164 |
| 4,547,243 | 10/1985 | Brody | 156/164 |
| 4,573,986 | 3/1986 | Minetola et al. | 156/291 |
| 4,585,507 | 4/1986 | Bradley | 156/164 |
| 4,634,482 | 1/1987 | Lammers | 156/291 |
| 4,642,150 | 2/1987 | Stemmler | 156/164 |

FOREIGN PATENT DOCUMENTS

| | | | |
|---|---|---|---|
| 1186288 | 4/1985 | Canada | 156/164 |
| 909427 | 10/1962 | United Kingdom | 239/298 |

Primary Examiner—Jerome Massie
Attorney, Agent, or Firm—Tilton, Fallon, Lungmus & Chestnut

[57] ABSTRACT

Method and apparatus for applying leg elastic to an elongated moving web adapted to provide a sequence of diapers wherein adhesive is continuously applied by a first air nozzle and shifted intermittently by means of a second air nozzle angularly related to the first air nozzle.

14 Claims, 11 Drawing Figures

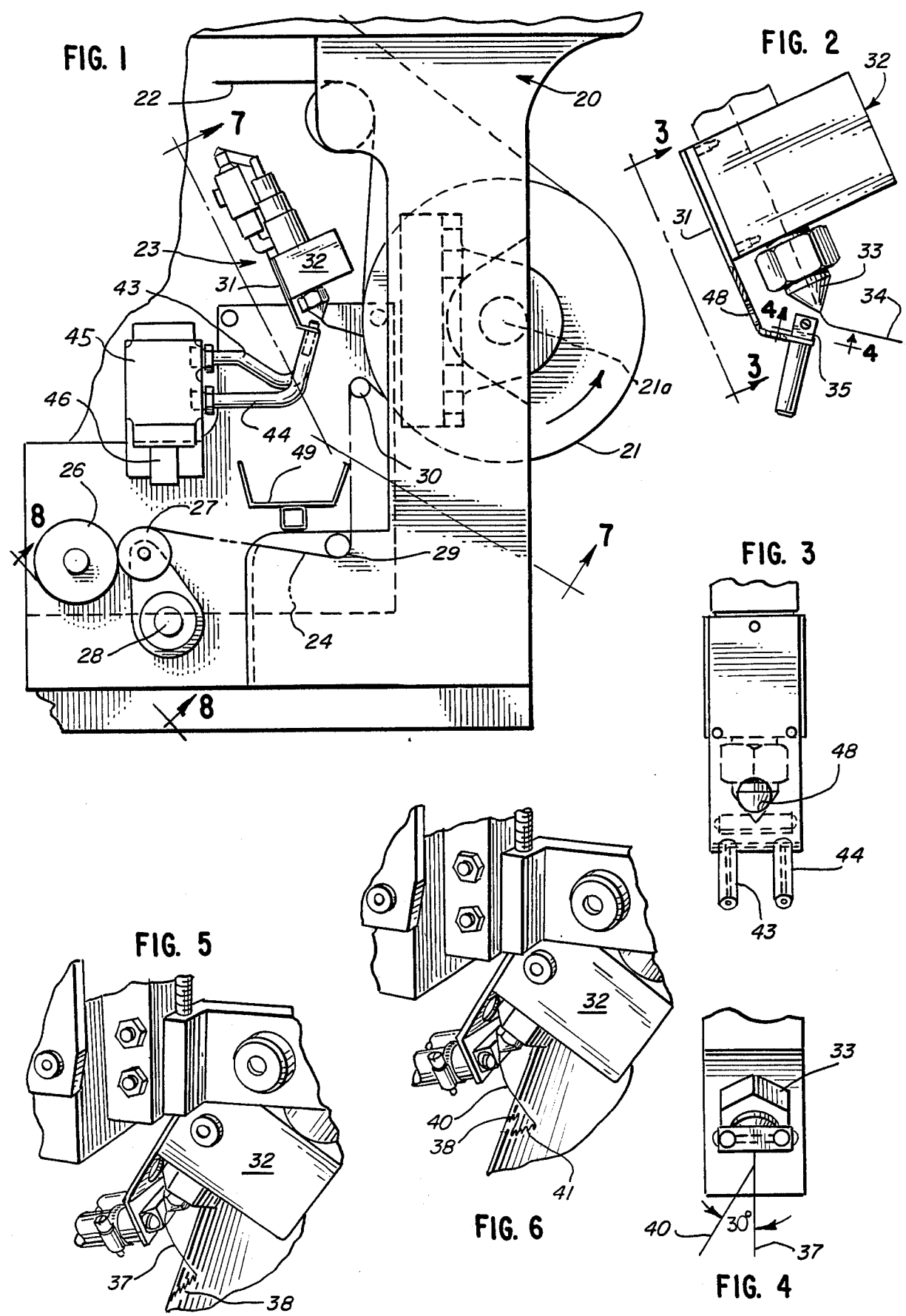

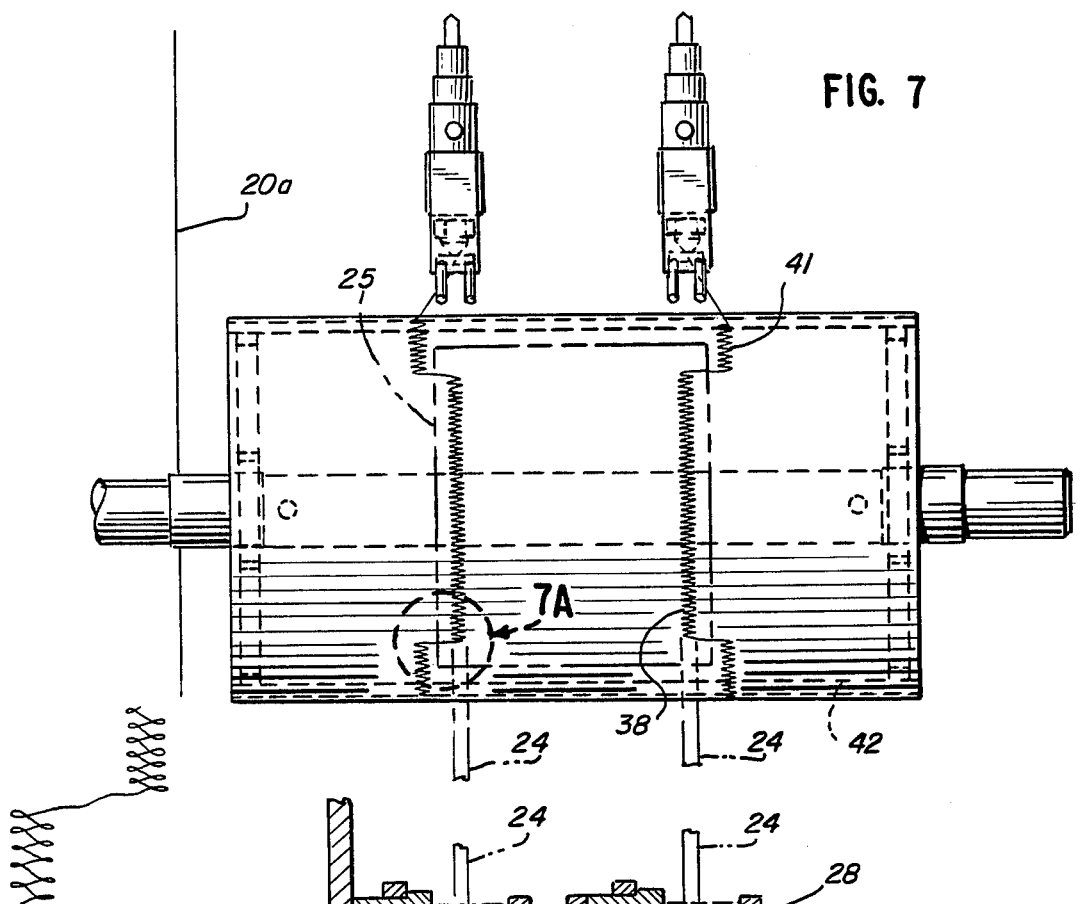
FIG. 7
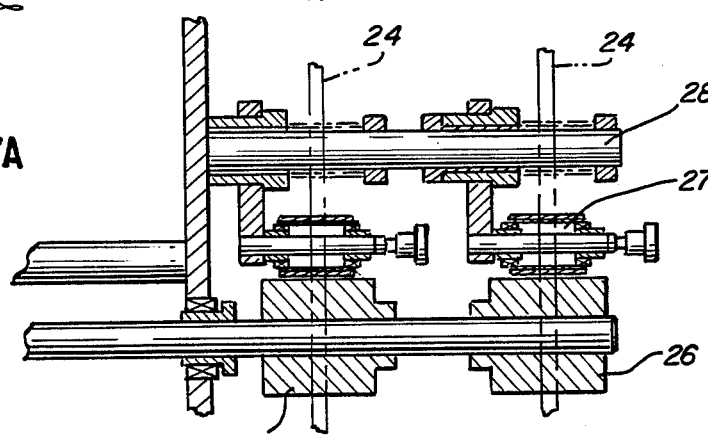
FIG. 7A
FIG. 8
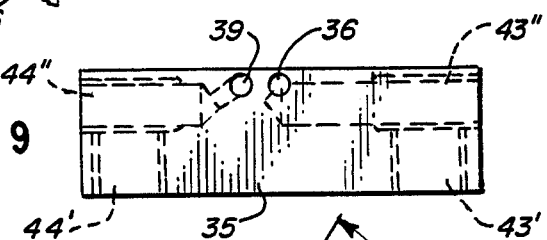
FIG. 9
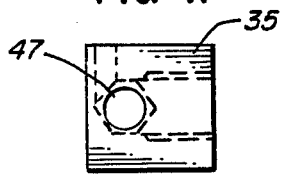
FIG. 11
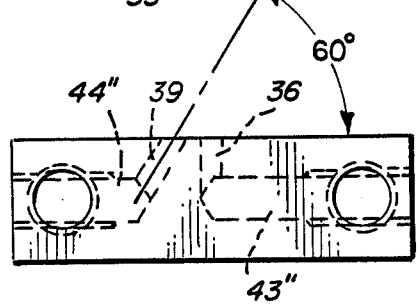
FIG. 10

METHOD AND APPARATUS FOR MAKING ELASTIC DIAPERS

BACKGROUND AND SUMMARY OF INVENTION

This invention relates to a method and apparatus for making elastic diapers and, more particularly, for continuously applying adhesive to the moisture-impervious web of the disposable diaper in such a way that the ends of the elastic ribbons forming the leg bands are unadhered and can, therefore, "snap back" within the diaper. As such it is an improvement on co-owned Bradley and Merkatoris U.S. Pat. No. 4,585,507, the teachings of which are incorporated herein by this express reference.

The basic teaching for the manufacture of an elastic leg band diaper is found in U.S. Pat. No. 4,081,031 and consists of stretching the elastic ribbons, maintaining tension therein, and intermittently applying adhesive to selected portions of the elastic corresponding to the contractable leg portion of the diaper. The '507 patent was directed to apparatus which avoided the drawbacks of intermittent adhesive application. Other patents which were concerned with continuous adhesive application were U.S. Pat. Nos. 4,300,967 and 4,353,762 but which had other disadvantages as discussed in '507. In both of these cases, there was a "canceling out" of the activity of the adhesive.

Another expedient employed by the art to "unadhere" spaced portions of the leg band elastic is seen in U.S. Pat. No. 4,547,243 where, although the adhesive was applied continuously, the amount was reduced cyclically to achieve "snap back". But this again required special equipment to handle the modulation.

In contrast to the foregoing, the instant invention is inexpensive and reliable in both installation and operation. Essentially, it provides for continuously applying adhesive along a first longitudinally extending line and intermittently shifting the adhesive laterally to a second line. This is achieved advantageously by a pair of nozzles, i.e., air flow passages, which are angularly related and with a valve to control the air flow in at least one of the passages. The invention is particularly advantageous in connection with applying adhesive to a web about to be engaged by a non-rubber, i.e., elastomer ribbon. When such ribbons were used in the oscillating fork of '507, they tended to remain in V-folded condition. Other advantages of the invention may be seen in the ensuing specification.

The invention is described in conjunction with an illustrative embodiment in the accompanying drawing in which FIG. 1 is a side elevational view of apparatus embodying the teaching of this invention;

FIG. 2 is an enlarged fragmentary side elevational view of the adhesive and air nozzle portion of FIG. 1 as seen in the upper left central portion thereof;

FIG. 3 is a rear elevational view such as would be seen along the sight line 3—3 of FIG. 2;

FIG. 4 is essentially a bottom elevational view the apparatus of FIG. 2 as seen along the sight line 4—4 applied thereto;

FIG. 5 is a fragmentary perspective view of the apparatus of the invention in one mode of operation, i.e., with the air stream from one nozzle directing the adhesive stream along a first longitudinally extending line on the moisture-impervious web;

FIG. 6 is a view similar to FIG. 5 but showing the alternate mode of operation wherein the other nozzle is operative to shift the adhesive line laterally;

FIG. 7 is an end elevational view such as would be seen along the sight line 7—7 of FIG. 1, FIG. 7A being an enlargement of the encircled portion of FIG. 7;

FIG. 8 is another end elevational view such as would be seen along the sight line 8—8 of FIG. 1;

FIG. 9 is an enlarged view of the air nozzle means seen in the upper portion of FIG. 7;

FIG. 10 is a view taken at right angles to the showing in FIG. 9; and

FIG. 11 is an end view of the showing in FIG. 10.

DETAILED DESCRIPTION

In the illustration given, and with reference first to FIG. 1, the numeral 20 designates generally the frame of the diaper-producing machine. Inasmuch as a good part of the machine consists of rolls, a pair of side frames are usually provided. Mounted for rotation within the frame 20 is a large roll or drum 21 which also can be seen in FIG. 7. At the extreme left of FIG. 7, one of the side frames is schematically represented by a vertical line 20a.

Returning to FIG. 1, the roll 21 is employed for uniting a pair of stretched elastic ribbons to a moisture-impervious web 22—see the upper left hand portion of FIG. 1. Conventionally, the web 22 is made of polyethylene. As the web 22 travels with the roll 21, being in partial wrapping engagement therewith, adhesive is applied to the web by means of an adhesive applying unit generally designated 23. Thereafter, a pair of laterally spaced apart ribbons of stretched elastic are applied. The ribbons are designated 24 and the arrangement of the two ribbons can be seen in the space between FIGS. 7 and 8.

This invention is not concerned with the remaining steps in the manufacture of disposable diapers. However, for the sake of completeness, the overall procedure is described. After the moisture impervious web is advanced through an adhesive applying station to lay down a pair of longitudinally-extending, laterally spaced-apart stripes of adhesive, and stretched elastic ribbons are applied to the adhesive stripes, a series of fluff batts (one of which is seen in the central portion of FIG. 7) is subsequently superposed on the moisture-impervious web in longitudinally spaced relation as indicated schematically at 25. Thereafter, a moisture-pervious web is adhered to the moisture-impervious web 22 to cover the fluff batts, thereby providing a continuous sequence of diapers. Lastly, the webs and the two ribbons are severed between the fluff batts to provide discrete diapers.

The elastic ribbons are provided from a roll or rolls (not shown) and are tensioned between a pair of axially aligned feedrolls 26 and nip rolls 27. These also can be seen in FIG. 8 and the tensioning is achieved by rotating the nip roll at a surface speed slower than the surface speed of the roll 21. Also seen in FIGS. 1 and 7 is a pivot shaft 28 which supports the nip rolls 27 to ensure proper pressure between the nip rolls 27 and feedrolls 26. After the ribbons have been tensioned by passing through the nip between the rolls 26 and 27, they pass around idlers 29 and 30 before being applied to the now adhesive-equipped polyethylene web 22.

ADHESIVE APPLYING STATION

Shortly after the web 22 (see FIG. 1) engages the roll 21, it passes through an adhesive applying station which includes the adhesive applying means generally designated 23. As can be seen from the central left hand portion of FIG. 1, the adhesive applying unit includes an angled bracket 31-seen in larger scale in FIG. 2. Secured to the bracket 31 is an adhesive supplying means generally designated 32 and which may be of conventional construction. For example, the unit illustrated is a glue gun model EP—25 provided by Meltex Corporation of Peachtree City, Ga. The adhesive supply means 32 includes a gear pump which is synchronized with the machine speed, i.e., the speed of advance of the polyethylene web 22, so as to deliver a continuous stream of adhesive from the adhesive supplying nozzle 33—see FIG. 2.

The invention is particularly concerned with the means for changing the direction of the adhesive stream issuing from the nozzle 33—the path of the adhesive stream being designated 34 in FIG. 2. The direction of the air stream is controlled by means of an air supply unit 35 which also can be seen in FIGS. 9-11. The unit 35 is essentially a rectangular block provided with certain air passages to direct the adhesive stream in two directions, both however being generally in the same plane. For example, when air is used from the passage 36 (see FIG. 10) the adhesive follows the path 37—see FIG. 4—and results in a stripe 38—see FIG. 7.

Intermittently, air is supplied through the passage 39—again see FIG. 10—which results in directing the adhesive stream at a different angle as seen at 40 in FIG. 4. This results in off-setting the adhesive stripe to the position 41 in FIG. 7. Thereafter, when the ribbons 24 are laid down, they are unadhered at the ends of the diapers, i.e., in the positions 41, so that after transverse severence of the webs and ribbons which would occur approximately along the transverse lines 42, the unsecured ends of the ribbons will "snap back" inside the diaper proper.

The two modes of operation of the air supply means can be seen in FIGS. 5 and 6 which are perspective views of the prototype machine and wherein FIG. 5 shows the operation where the stripe is laid down in the position 38 and FIG. 6 shows the operation where the stripe is laid down in the position 41. Exemplary of the operation is the ensuing example.

EXAMPLE

The prototype machine operated at a speed of 600 feet per minute for the polyethylene web 22 which would result in 400 diapers per minute with each of the baby diapers being 18" in length. As indicated above, the glue gun was of Meltex manufacture and the air was supplied at 40 psi. This value was selected because it is commonly available in most manufacturing plants. Air pressure was supplied to the block 35 by means of hoses 43 and 44 and the switching of the air pressure from one hose to the other was controlled by a solenoid valve 45 having an air supply line 46—see the left central portion of FIG. 1.

The air line 43 is connected to the inlet passage 43'. The passage 43' is connected to a second passage 43". As can be seen in FIG. 9 and, as can be seen in FIG. 10, the passage 43" connects with the nozzle-providing passage 36.

In similar fashion, the air hose 44 is connected by means of passage 44' (see FIG. 9) and passage 44" (see also FIG. 10) with the nozzle providing passage 39. Each of the passages are suitably drilled and the ends of the passages 43" and 44" are closed by plugs as at 47 (see FIG. 11). The block 35 is advantageously constructed of brass and the nozzle-providing passages 36, 39 have a bore of 0.055 inches. This size passage provides the advantageous entraining and drawing effect with 40 psi air pressure. With a passage having a diameter of 0.062 the adhesive stream caused to impinge upon the web 22 was too fine and with a passage bore of 0.035 inches, the stream was too thick.

The entraining and drawing effect can be appreciated from a consideration of FIG. 7A which is an enlargement of the transition portion of the adhesive stripes from a first longitudinally extending line to a second longitudinally extending line. The entraining and drawing effect of the air on the adhesive stream 37 or 40, as the case may be, results in a fine continuous line of adhesive which moves around within a band to provide a randomized pattern. This is similar to the spinneret action with which synthetic fibers are generated. Assisting in this action is a secondary supply of air which passes through the opening 48 in the bracket 31—compare FIGS. 2 and 3. Air is aspirated through the opening 48 by the air issuing from the passages 36 or 39 and assists in the above referred-to entraining and drawing effect.

As illustrated, it is advantageous to mount the adhesive applying means 23 at the 9 o'clock position (or the 3 o'clock position) so that any adhesive not directed onto the web 22 will fall into the drip pan 49. This also is advantageous in the case of a temporary loss of air pressure so that any adhesive emanating from the nozzle 33 will not fall on the web 22 or the ribbons 24. The adhesive applied is a conventional adhesive for the manufacture of disposal diapers such as that available under No. 34-2881 from National Starch Company.

This adhesive is heated to about 350° F. and to a viscosity of about 1300 cps and if allowed to fall directly on the polyethylene web 22, would melt the web. If allowed to fall directly on the ribbons 24, the hot adhesive would break the ribbons. To assist in controlling the temperature of the web 22, the roll 21 is a "chill" roll analogous to that described in co-owned U.S. Pat. No. 4,417,935. In the '935 patent, a foamed adhesive was described so as to limit the amount of heat transfer from the adhesive to the polyethylene web. The surface of the roll 21 can be maintained at or below ambient temperature web. The surface of the roll 21 can be maintained at or below ambient temperature by means of a cooling fluid introduced along the axis 21a of the roll 21, the roll 21 being mounted for rotation about a horizontal axis. As indicated previous, I have found it advantageous to locate the adhesive applying means 23 in a position so that the adhesive stream 34 is generally in the same horizontal plane as that including the axis 21a.

In the prototype machine, the distance between the outlets of the passages 36, 39 and the tip of the nozzle 33 was about ⅛ inch. This may be varied somewhat as well as the bores of the passages 36, 39 depending upon the pressure of the supply air and the temperature and viscosity of the adhesive.

While in the foregoing specification a detailed description of an embodiment of the invention has been set down for the purpose of illustration, many variations in the details hereingiven may be made by those skilled in the art without departing from the spirit and scope of the invention.

I claim:

1. In a method applying a leg elastic ribbon to an elongated moisture-impervious web adapted to form a series of diapers, the steps of delivering a continuous stream of adhesive to a point adjacent to but spaced from said web, directing a first air stream adjacent said adhesive stream to entrain and draw said adhesive stream onto said web along a first longitudinal line, intermittently directing a second air stream adjacent said adhesive stream at an angle to said first air stream to shift said adhesive stream laterally to a second longitudinal line, and applying a stretched elastic ribbon to said web on said first longitudinal line.

2. The method of claim 1 in which said first air stream is stopped during the application of said second air stream.

3. The method of claim 2 in which each air stream spins said adhesive stream into a thin filiment continuously and randomly which is deposited on said web.

4. The method of claim 1 in which each air stream has a velocity sufficient to entrain and draw said adhesive stream to provide adhesive in a pattern on said web having a width approximating the width of said elastic ribbon.

5. In a method of making disposable diapers wherein a moisture-impervious web is advanced through an adhesive applying station to lay down a pair of longitudinally-extending, laterally spaced stripes of adhesive, applying stretched elastic ribbons to said adhesive stripes, fluff batts are superposed on said moisture-impervious web in longitudinally spaced relation, a moisture-pervious web is adhered to said moisture-impervious web to cover said fluff batts to provide a continuous sequence of diapers and wherein said webs and ribbons are severed between fluff batts to provide discrete diapers, the improvement of positioning a pair of air supply nozzles adjacent an adhesive supply nozzle in said adhesive applying station, said air supply nozzles being in angled relation to each other, delivering an air stream from one air supply nozzle to direct adhesive from said adhesive supply nozzle to a first position on said moisture-impervious web and intermittently delivering an air stream from the other air supply nozzle to laterally shift the direction of said adhesive to a second position, said ribbons being applied to adhesive in said first position.

6. The method of claim 5 in which adhesive in said second position overlaps the space between fluff batts.

7. The method of claim 5 in which said webs and ribbons are severed along a transversely extending line positioned in each space between adjacent fluff batts, adhesive in said second position extending on each side of said transversely extending line.

8. Apparatus for applying adhesive to a web for adhering an elastic ribbon thereto for use as part of a disposal diaper comprising:
a frame, a roll rotatably mounted on said frame, first means associated with said roll for feeding a web for travel with said roll in partial wrapping engagement therewith, second means associated with said roll for feeding a pair of stretched elastic ribbons for travel on said web after adhesive has been applied to said web,
an adhesive applying unit on said frame for each ribbon positioned closely to but spaced from said roll for applying adhesive to said web before said ribbons engage said web, each adhesive unit including bracket means mounted on said frame, adhesive delivery means on said bracket means including a nozzle for delivering a thin continuous stream of adhesive, and
air nozzle means on said bracket means having a pair of passages directed adjacent said adhesive stream to cause the same to impinge on said web, said passages being angularly related so that the air stream from one passage lays down a pattern of adhesive along a first line extending longitudinally in the direction of web travel and the air stream from the other passage lays down a pattern of adhesive along a second line extending longitudinally in the direction of web travel spaced laterally from the first line, and control means operatively associated with said air nozzle means for intermittently delivering an air stream through said other passage in synchronization with a diaper length whereby when said ribbon is aligned with said first line and the adhesive pattern in said second line overlaps the end of one diaper length and the beginning of the next diaper length, said ribbon is not adhered to the diaper ends.

9. The apparatus of claim 8 in which said bracket means is equipped with an opening adjacent said air nozzle means to facilitate aspiration of air therethrough by said air streams.

10. The apparatus of claim 8 in which said air nozzle means includes a block having said air passages arranged therein at about a 30 degree angle relative to each other.

11. The apparatus of claim 8 in which said roll is mounted for rotation about a horizontal axis, said passages being disposed in said air nozzle to deliver said air streams generally in a horizontal plane containing said roll axis whereby adhesive not entrained by said air stream falls by gravity free of said roll.

12. The apparatus of claim 8 in which said roll is equipped with means for maintaining the roll surface below ambient temperature.

13. Apparatus for intermittently adhering an elastic leg band to a diaper web comprising a frame, means on said frame for advancing said web along a predetermined path, an adhesive delivery nozzle positioned on said frame adjacent to but spaced from said path, air nozzle means on said frame adjacent to said adhesive delivery nozzle but on the side thereof opposite said path, said air nozzle means being adapted to direct an adhesive stream from said adhesive nozzle against said web, means operatively associated with said air nozzle means for intermittently changing the direction of the air stream issuing therefrom, and means for applying said ribbon to said web.

14. The apparatus of claim 13 in which said air nozzle means includes a pair of angularly related air flow passages sized and spaced from said adhesive delivery nozzle to develop entrained and directed flow in said adhesive stream issuing from said adhesive delivery nozzle.

* * * * *